(12) United States Patent
Ghoshal

(10) Patent No.: US 11,826,173 B2
(45) Date of Patent: Nov. 28, 2023

(54) SYSTEM AND METHOD TO COMPENSATE FOR TRANSIT-INDUCED VIBRATION WHEN DETECTING HEART RATE USING RADAR SENSORS

(71) Applicant: ADVANCED TELESENSORS, INC., Austin, TX (US)

(72) Inventor: Sajol Ghoshal, Austin, TX (US)

(73) Assignee: ADVANCED TELESENSORS, INC., Austin, TX (US)

( * ) Notice: Subject to any disclaimer, the term of this patent is extended or adjusted under 35 U.S.C. 154(b) by 234 days.

(21) Appl. No.: 17/086,897

(22) Filed: Nov. 2, 2020

(65) Prior Publication Data

US 2021/0128068 A1 May 6, 2021

Related U.S. Application Data

(60) Provisional application No. 62/928,490, filed on Oct. 31, 2019.

(51) Int. Cl.
*A61B 5/00* (2006.01)
*A61B 5/024* (2006.01)
*A61B 5/05* (2021.01)

(52) U.S. Cl.
CPC ............ *A61B 5/721* (2013.01); *A61B 5/0004* (2013.01); *A61B 5/02444* (2013.01); *A61B 5/05* (2013.01);
(Continued)

(58) Field of Classification Search
None
See application file for complete search history.

(56) References Cited

U.S. PATENT DOCUMENTS

| 4,513,748 A | 4/1985 | Nowogrodzki et al. |
| 4,958,638 A | 9/1990 | Sharpe et al. |

(Continued)

FOREIGN PATENT DOCUMENTS

EP 2537462 A1 12/2012

OTHER PUBLICATIONS

Jarchi et al., "Description of a database containing wrist PPG signals recorded during physical exercise with both accelerometer and gyroscope measures of motion", Data, 2017, 2, 1, pp. 1-13. (Year: 2017).*

Lazaro, A. et al., "Analysis of Vital Signs Monitoring Using an IR-UWB Radar," Progress in Electromagnetics Research, vol. 100, 2010, pp. 265-284.

(Continued)

*Primary Examiner* — Yi-Shan Yang
(74) *Attorney, Agent, or Firm* — Withrow & Terranova, P.L.L.C.; Vincent K. Gustafson

(57) ABSTRACT

A system and method to compensate for transit-induced vibration when detecting heart rate using radar sensors is provided. Embodiments provide a radio frequency RF sensor for heart rate detection when a subject is in transit (e.g., in a vehicle and/or subject to human-induced motion), where the RF sensor is designed to cancel vibration noise while preserving a cardiac signal in a radar response so that a heart rate, respiratory rate, and related physiological parameters of a subject under test can be extracted. In some examples, a heart rate variability (HRV) and/or state of the subject under test can be derived from these physiological parameters as well. The RF sensor with vibration cancellation can be installed in multiple locations in a vehicle, including a car seat, a steering wheel, a roof of the vehicle, a visor, or a rearview mirror; alternatively, the components may be held or worn by a subject, or arranged proximate to a subject.

18 Claims, 10 Drawing Sheets

(52) U.S. Cl.
CPC .... *A61B 5/6893* (2013.01); *A61B 2560/0223* (2013.01); *A61B 2562/0219* (2013.01)

(56) References Cited

U.S. PATENT DOCUMENTS

| | | | |
|---|---|---|---|
| 5,760,687 | A | 6/1998 | Cousy |
| 6,122,537 | A | 9/2000 | Schmidt |
| 6,753,780 | B2 | 6/2004 | Li |
| 7,811,234 | B2 | 10/2010 | McGrath |
| 9,492,099 | B2 | 11/2016 | Gamble et al. |
| 2005/0143667 | A1 | 6/2005 | Park et al. |
| 2007/0060827 | A1 | 3/2007 | Kobayashi et al. |
| 2008/0119716 | A1 | 5/2008 | Boric-Lubecke et al. |
| 2008/0146944 | A1 | 6/2008 | Tao et al. |
| 2009/0203972 | A1 | 8/2009 | Heneghan et al. |
| 2009/0227882 | A1 | 9/2009 | Foo |
| 2009/0278728 | A1 | 11/2009 | Morgan et al. |
| 2015/0025917 | A1* | 1/2015 | Stempora ............ G06V 40/193 705/4 |
| 2019/0043064 | A1* | 2/2019 | Chin ................. G06Q 30/0201 |
| 2019/0250261 | A1* | 8/2019 | Itkin ........................ H04B 1/44 |

OTHER PUBLICATIONS

Li, Chang, "Non-Contract Estimation of Respiration and Heartbeat Rate Using Ultra-Wideband Signals," Master's Thesis, Aug. 29, 2008, Virginia Polytechnic Institute and State University, 121 pages.

Mikhelson, Ilya V. et al., "Remote Sensing of Heart Rate and Patterns of Respiration on a Stationary Subject Using 94 GHz Millimeter Wave Interferometry," IEEE Transactions on Biomedical Engineering, vol. 58, No. 6, Feb. 4, 2010, IEEE, p. 1-7.

Perry, Christopher M. et al., "Non-Contact Vital Sign Monitoring via Ultra Wideband Radar, Infrared Video, and Remote Photoplethysmography: Viable Options for Space Exploration Missions," National Aeronautics and Space Administration, May 2011, Johnson Space Center, 15 pages.

Rahman, Mohammad Shaifur et al., "Extended Kalman Filter for Rate Estimation in Doppler Radar Cardiopulmonary Monitoring System," International Journal of Bio-Science and Bio-Technology, vol. 4, No. 4, Dec. 2012, Science & Engineering Research Support society, pp. 95-105.

Scalise, Lorenzo, "Non Contact Heart Monitoring," Advances in Electrocardiograms—Methods and Analysis, Chapter 4, Millis, Richard, M., (Ed.) Jan. 25, 2012, InTech, pp. 81-106.

* cited by examiner

SYSTEM AND METHOD TO COMPENSATE FOR TRANSIT-INDUCED VIBRATION WHEN DETECTING HEART RATE USING RADAR SENSORS

CROSS-REFERENCE TO RELATED APPLICATIONS

This application claims priority to U.S. Provisional Patent Application No. 62/928,490 filed on Oct. 31, 2019, wherein the entire contents of the foregoing application are hereby incorporated by reference herein.

FIELD OF THE DISCLOSURE

This application relates to remote sensing of physiological parameters of animals, such as humans.

BACKGROUND

The state of drivers on roadways is an area of concern which has become more important in recent years as more semi-autonomous vehicles have emerged. The driver state can be extracted from heart rate variability (HRV), which is based on interbeat intervals from a driver's heart rate and pulse position information. However, to successfully extract heart rate and HRV while a vehicle is moving requires sophisticated signal processing and cancellation techniques to suppress road noise while preserving the cardiac signal. Additional challenges in extracting heart rate and HRV information may occur in a non-vehicular context when a person is in transit (e.g., while exercising or otherwise in motion) proximate to a sensor, which may be held (e.g. hand-held) by the person, worn by the person, or otherwise placed proximate to the person.

SUMMARY

A system and method to compensate for transit-based (e.g., vehicular) vibration when detecting heart rate using radar sensors is provided. A heart rate detection system is presented which utilizes high frequency radio frequency (RF) signals transmitted to and reflected back from the body of a mammal (e.g., RF signals reflected from the upper torso of a human subject under test where the heart is located). The reflected signal is captured with an antenna, processed, and analyzed to extract the heart rate and/or respiratory rate. This reflected signal is, however, corrupted by movement artifacts that are naturally picked up when the mammal moves in the course of its normal movement. Algorithms are applied to the reflected signal to minimize and/or eliminate the movement artifacts separating a cardiac signal from the movement information.

When the heart rate detection system is used in an automobile or other moving vehicle, a human driver or passenger (e.g., the subject under test) remains generally still while a sensor of the system affixed to the vehicle is subject to vibration noise from vehicle engine vibration and road noise (e.g., bumps, turns, tire noise). This vibration noise makes extraction of the cardiac signal of the subject under test extremely difficult. This vibration signal can be 1,000 times higher than the cardiac signal that needs to be detected. Likewise, when the heart rate detection system is arranged proximate to a subject in transit (whether or not in a vehicular context), vibration incident to human motion may likewise render it challenging to extract a cardiac signal of the subject under test.

Thus, embodiments of the present disclosure provide an RF sensor for heart rate detection designed to cancel the vibration noise while preserving the cardiac signal so that a heart rate, respiratory rate, and related physiological parameters can be extracted. In some examples, a heart rate variability (HRV) and/or state of the subject under test can be derived from these physiological parameters as well. An RF sensor with vibration cancellation can be installed in multiple locations in a vehicle, including a car seat, a steering wheel, a roof of a vehicle, a visor, or a rearview mirror. Similarly, an RF sensor with vibration cancellation may be configured to be held by a user, worn by a user, or otherwise placed proximate to a user in transit, whether due to human motion and/or vehicular motion.

In one aspect, the disclosure relates to a method for detecting heart rate of a subject under test in exposure to transit-based vibration. The method includes transmitting an RF signal toward the subject under test. The method further includes receiving a response signal from an RF receive signal path, the response signal comprising a reflection of the RF signal. The method further includes receiving a motion signal from a gyroscope signal path. The method further includes cancelling a vibration component of the response signal using the motion signal to produce a corrected response signal. The method further includes extracting a cardiac signal of the subject under test from the corrected response signal.

In certain embodiments, the subject under test is in a vehicle, the transmitting of the RF signal is performed with a vehicle-mounted RF transmitter, the receiving of the response signal is performed with a vehicle-mounted RF receiver, and the receiving of the motion signal from the gyroscope signal path is performed with a vehicle-mounted gyroscope element.

In certain embodiments, the subject under test is not in a vehicle; the transmitting of the RF signal is performed with a RF transmitter that is held by the subject, worn by the subject, or placed proximate to the subject; the receiving of the response signal is performed with a RF receiver that is held by the subject, worn by the subject, or placed proximate to the subject; and the receiving of the motion signal from the gyroscope signal path is performed with a gyroscope element that is held by the subject, worn by the subject, or placed proximate to the subject.

In certain embodiments, the method further includes equalizing the gyroscope signal path to the RF receive signal path. In certain embodiments, the equalizing the gyroscope signal path is provided by an adaptive equalizer. In certain embodiments, the method further includes calibrating the adaptive equalizer with the vehicle operating and no human subject present to further equalize the gyroscope signal path to the RF receive signal path. In certain embodiments, the method further includes recalibrating the adaptive equalizer with the vehicle operating and a human subject present. In certain embodiments, the adaptive equalizer digitally filters the motion signal from the gyroscope signal path using a set of tap weights trained with a learning algorithm.

In certain embodiments, the RF receive signal path comprises an RF antenna, an analog front end, and an analog to digital converter (ADC).

In another aspect, the disclosure relates to a method for detecting heart rate of a subject under test in transit, whether due to human and/or vehicular motion. The method includes transmitting an RF signal toward the subject under test. The method further includes receiving a response signal from an RF receive signal path, the response signal comprising a reflection of the RF signal. The method further includes receiving a motion signal from a gyroscope signal path. The method further includes cancelling a transit-related vibration component of the response signal using the motion signal to produce a corrected response signal. The method further includes extracting a cardiac signal of the subject under test from the corrected response signal.

In another aspect, the disclosure relates to an RF sensor. The RF sensor includes a substrate; an RF transceiver mounted to the substrate; a gyroscope mounted to the substrate; and a processing device coupled to the RF transceiver and the gyroscope. The processing device is configured to cause the RF transceiver to transmit an RF signal toward a subject under test; receive a response signal comprising a reflection of the RF signal from the RF transceiver; monitor a motion signal from the gyroscope; cancel a vibration component of the response signal using the motion signal from the gyroscope to produce a corrected response signal; and extract a cardiac signal of the subject under test from the corrected response signal.

In certain embodiments, the RF sensor further includes an analog front end coupled to the RF transceiver and configured to receive, filter, and amplify an RF receive signal to provide an analog response signal. In certain embodiments, the RF sensor further includes an ADC coupled to the analog front end and configured to digitally convert the analog response signal to the response signal provided to the processing device.

In certain embodiments, the RF sensor further includes an adaptive equalizer coupled to the gyroscope and configured to apply a distortion to the motion signal matched to a receive path between an antenna coupled to the RF transceiver and the processing device. In certain embodiments, the adaptive equalizer is further configured to apply the distortion to the motion signal matched to the distortion of an analog front end coupled to the RF transceiver. In certain embodiments, the adaptive equalizer is trained after installation of the RF sensor in a vehicle. In certain embodiments, training the adaptive equalizer comprises minimizing a difference between the vibration component from the receive path and the motion signal provided to the processing device with the vehicle operating and no human subject present. In certain embodiments, training the adaptive equalizer comprises minimizing a difference between the vibration component from the receive path and the motion signal provided to the processing device with the vehicle operating and a human subject present.

In another aspect, the disclosure relates to a heart rate detection system. The heart rate detection system includes a vehicle comprising a seat and an RF sensor coupled to the seat. The RF sensor includes a substrate; an RF transceiver mounted to the substrate; a gyroscope mounted to the substrate; and a processing device coupled to the RF transceiver and the gyroscope. The processing device is configured to: cause the RF transceiver to transmit an RF signal toward a subject under test; receive a response signal comprising a reflection of the RF signal from the RF transceiver; monitor a motion signal from the gyroscope; cancel a vibration component of the response signal using the motion signal from the gyroscope to produce a corrected response signal; and extract a cardiac signal of the subject under test from the corrected response signal.

In certain embodiments, the heart rate detection system further includes a network interface device configured to couple to a vehicle computer, relay, or sensor. In certain embodiments, the RF sensor further comprises an adaptive equalizer coupled to the gyroscope and configured to apply a distortion to the motion signal matched to a receive path between an antenna coupled to the RF transceiver and the processing device. In certain embodiments, the adaptive equalizer comprises a multi-tap digital filter trained after installation of the RF sensor in the vehicle. In certain embodiments, the processing device is further configured to adjust the distortion applied to the motion signal based on a vehicle status signal received from the vehicle computer, relay, or sensor.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

Figure 1A:
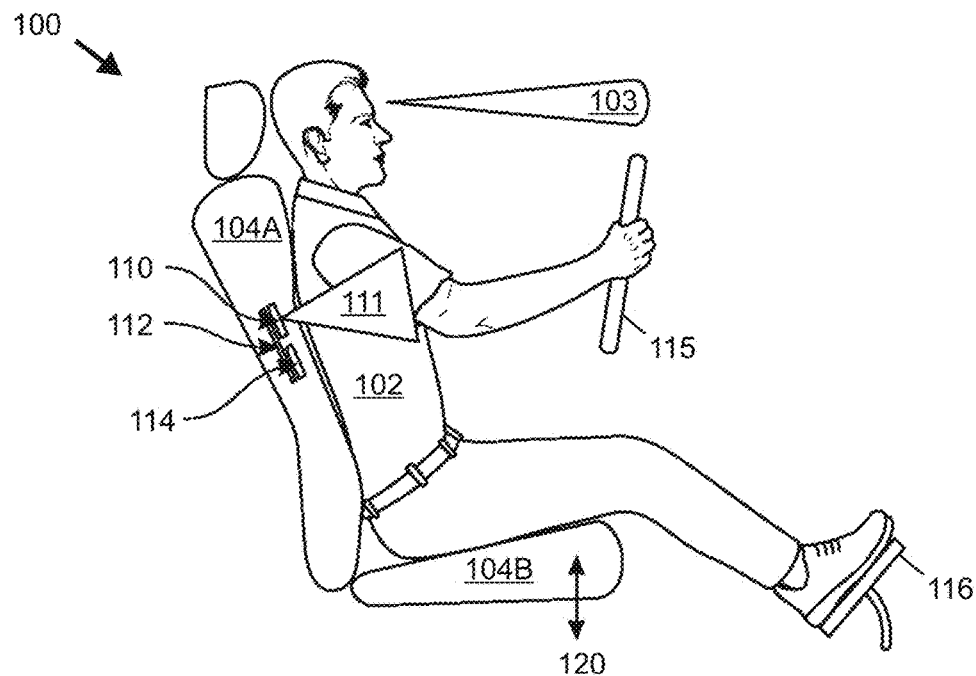
FIG. 1A is a schematic diagram of an exemplary heart rate detection system implemented in a seat of a vehicle.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A system and method to compensate for transit-based (e.g., vehicular) vibration when detecting heart rate using radar sensors is provided. A heart rate detection system is presented which utilizes high frequency radio frequency (RF) signals transmitted to and reflected back from the body of a mammal (e.g., RF signals reflected from the upper torso of a human subject under test where the heart is located). The reflected signal is captured with an antenna, processed, and analyzed to extract the heart rate and/or respiratory rate. This reflected signal is, however, corrupted by movement artifacts that are naturally picked up when the mammal moves in the course of its normal movement. Algorithms are applied to the reflected signal to minimize and/or eliminate the movement artifacts separating a cardiac signal from the movement information.

In certain embodiments, the subject under test is in a vehicle, the transmitting of the RF signal is performed with a vehicle-mounted RF transmitter, the receiving of the response signal is performed with a vehicle-mounted RF receiver, and the receiving of the motion signal from the gyroscope signal path is performed with a vehicle-mounted gyroscope element.

In certain embodiments, the subject under test is not in a vehicle; the transmitting of the RF signal is performed with a RF transmitter that is held by the subject, worn by the subject, or placed proximate to the subject; the receiving of the response signal is performed with a RF receiver that is held by the subject, worn by the subject, or placed proximate to the subject; and the receiving of the motion signal from the gyroscope signal path is performed with a gyroscope element that is held by the subject, worn by the subject, or placed proximate to the subject.

When the heart rate detection system is used in an automobile or other moving vehicle, a human driver or passenger (e.g., the subject under test) remains generally still while a sensor of the system affixed to the vehicle is subject to vibration noise from vehicle engine vibration and road noise (e.g., bumps, turns, tire noise). This vibration noise makes extraction of the cardiac signal of the subject under test extremely difficult. This vibration signal can be 1,000 times higher than the cardiac signal that needs to be detected. Similar challenges occur in a non-vehicular context when a person is in transit (e.g., while exercising or otherwise in motion) proximate to a sensor, which may be held (e.g. hand-held) by the person, worn by the person, or otherwise placed proximate to the person. In certain contexts, a person in transit may be subject to vibration caused by vehicular motion in addition to vibration caused by human movement (e.g., if a user is moving inside a bus or train car, or actively walking on a moving walkway).

Thus, embodiments of the present disclosure provide an RF sensor for heart rate detection designed to cancel one or more modes of transit-based vibration noise while preserving the cardiac signal so that a heart rate, respiratory rate, and related physiological parameters can be extracted. In some examples, a heart rate variability (HRV) and/or state of the subject under test can be derived from these physiological parameters as well. In certain embodiments, an RF sensor with vibration cancellation can be installed in multiple locations in a vehicle, including a car seat, a steering wheel, a roof of the vehicle, a visor, or a rearview mirror. In certain embodiments, an RF sensor with vibration cancellation may be held by a person, worn by a person, or arranged proximate to a person in transit, wherein such transit may be motivated by human movement and/or vehicular movement.

Doppler radar utilizes the theory that a reflected radar wave from a moving target will directly affect the frequency of the return signal. A radar wave reflected from a target moving in a periodic forward/backward motion will exhibit what can be classified as a phase shift relative to the periodic motion. When a heart beats inside the body of a mammal (e.g., a human), it produces a periodic motion on the surface of the torso or chest wall of the body. If the body reflecting the RF wave also exhibits non-cardiac motion, then the reflected signal will also contain another component indicated by the type and magnitude of motion. The phase shift of the received signal can be analyzed for cardiac and motion contents while filtering other noise components from the scene. If the motion originates from vibration or movement of the subject under test in the same frequency band as the cardiac activity, then the vibratory or motion component of the signal dominates the return signal and can mask the cardiac signal itself.

Systems and methods for remotely sensing physiologic (e.g., cardiac) data of subjects have been disclosed in U.S. Pat. Nos. 9,492,099; 7,811,234; and 7,272,431. U.S. Pat. No. 7,811,234 discloses a non-imaging method of remotely sensing cardiac-related data of a subject, the method including: transmitting a microwave signal to illuminate tissue of the subject; receiving a reflected microwave signal, the reflected microwave signal being a reflection of the microwave signal from illuminated tissue of the subject; processing the reflected microwave signal and analyzing an amplitude of the reflected microwave signal to determine changes in a reflection coefficient at an air-tissue interface of the subject's body resulting from changes in permittivity of the illuminated tissue of the subject, the changes in permittivity containing a static component and a time-varying component; and processing the time-varying component to provide cardiographic related data of the subject. U.S. Pat. No. 9,492,099 discloses systems and methods for remote sensing of physiologic activity, including cardiac activity and respiration rate, with signal processing schemes to provide improved reproducibility despite variation in relative position between RF components and a human subject, movement of a human subject, and/or presence of interfering signals. In certain embodiments, hardware and/or filtering schemes of U.S. Pat. No. 9,492,099 may be used in implementations of systems and methods disclosed herein.

FIG. 1A is a schematic diagram of an exemplary heart rate detection system 100 implemented (at least in part) in a seat (e.g., seatback 104A and/or seat cushion 104B) of a vehicle. The seatback 104A and 104B support a subject 102 under test, with the subject 102 being shown as grasping a steering wheel 115 (below a field of view 103 of the subject 102) and positioned to manipulate one or more pedals 116. The heart rate detection system includes an RF sensor 110 which compensates for vehicle vibration when detecting a heart rate of a subject 102 under test. The RF sensor 110 includes an RF transceiver (which may have an integrated transmitter and receiver, or may be replaced with separate RF transmitter and RF receiver components) and a gyroscope 114 mounted to a single substrate 112, such as a printed circuit board (PCB). Under a Doppler radar approach, the RF sensor 110 transmits an RF signal 111 toward the subject 102 under test and receives a response signal after reflection from the body of the subject 102 under test.

A cardiac signal 126 of the subject 102 under test exhibits a periodic motion on the surface of the torso or chest wall of the subject's body. The magnitude of the movement of the chest wall of the subject 102 is very small (e.g., 0.1 mm or less), and thus a phase modulation in the response signal is also very small, and requires a very low noise amplification to analyze the signal. However, when the vehicle operates, the seat (104A, 104B) and the subject 102 under test experience vibration 120 from an engine and other motions of the vehicle (e.g., road noise).

Figure 1B:
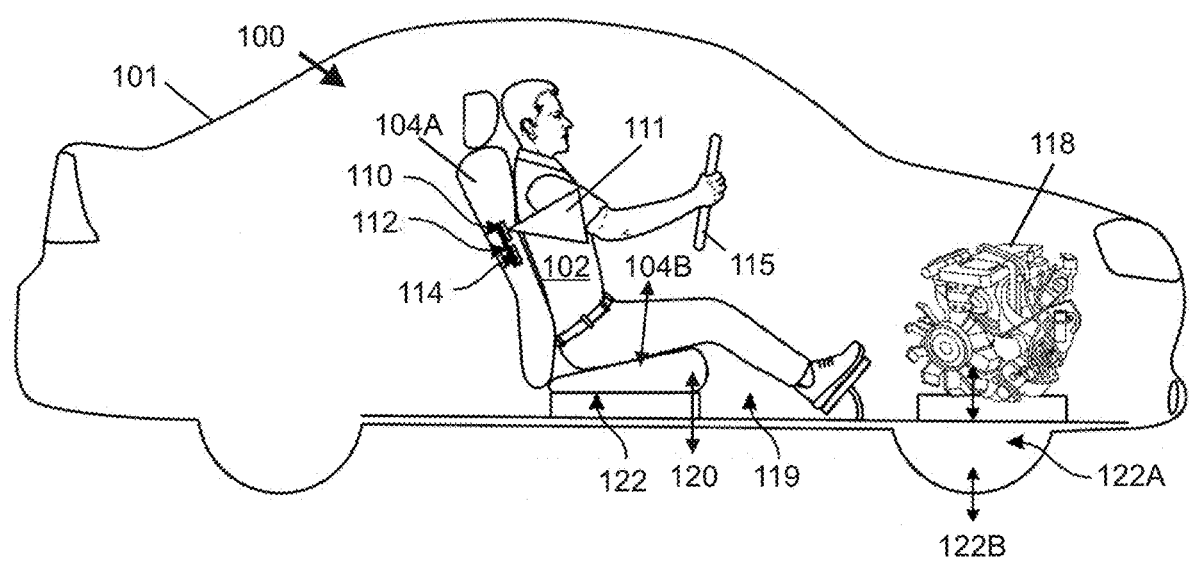
FIG. 1B is a schematic diagram of the heart rate detection system of FIG. 1A, illustrating vibration signals coupled to the seat through a chassis of the vehicle.

FIG. 1B is a schematic diagram of the heart rate detection system 100 of FIG. 1A in a vehicle 101, illustrating vibration signals coupled to the seat (e.g., seatback 104A and/or seat cushion 104B) through a chassis 119 of the vehicle 101. An engine 118 of the vehicle 101 may generate engine vibrations (also termed engine noise) 122A that are transmitted to the chassis 119, while road vibrations (also termed road noise) 122B are further transmitted to the chassis 119 of the vehicle 101. Combined vibrations 120 are transmitted through the chassis 119 and seat frame 122 into the seat cushion 104B and seatback 104 to the subject 102 under text. These vibrations 120 of the vehicle 101 transmitted to the subject 102 can cause a vibration component in the response signal received by the RF sensor 101 to swamp out the actual cardiac signal by multiple orders of magnitude. Thus, embodiments of the present disclosure cancel the significantly large vibration component of the response signal due to vehicle vibration so that the much smaller amplitude cardiac signal can be detected.

Figure 2:
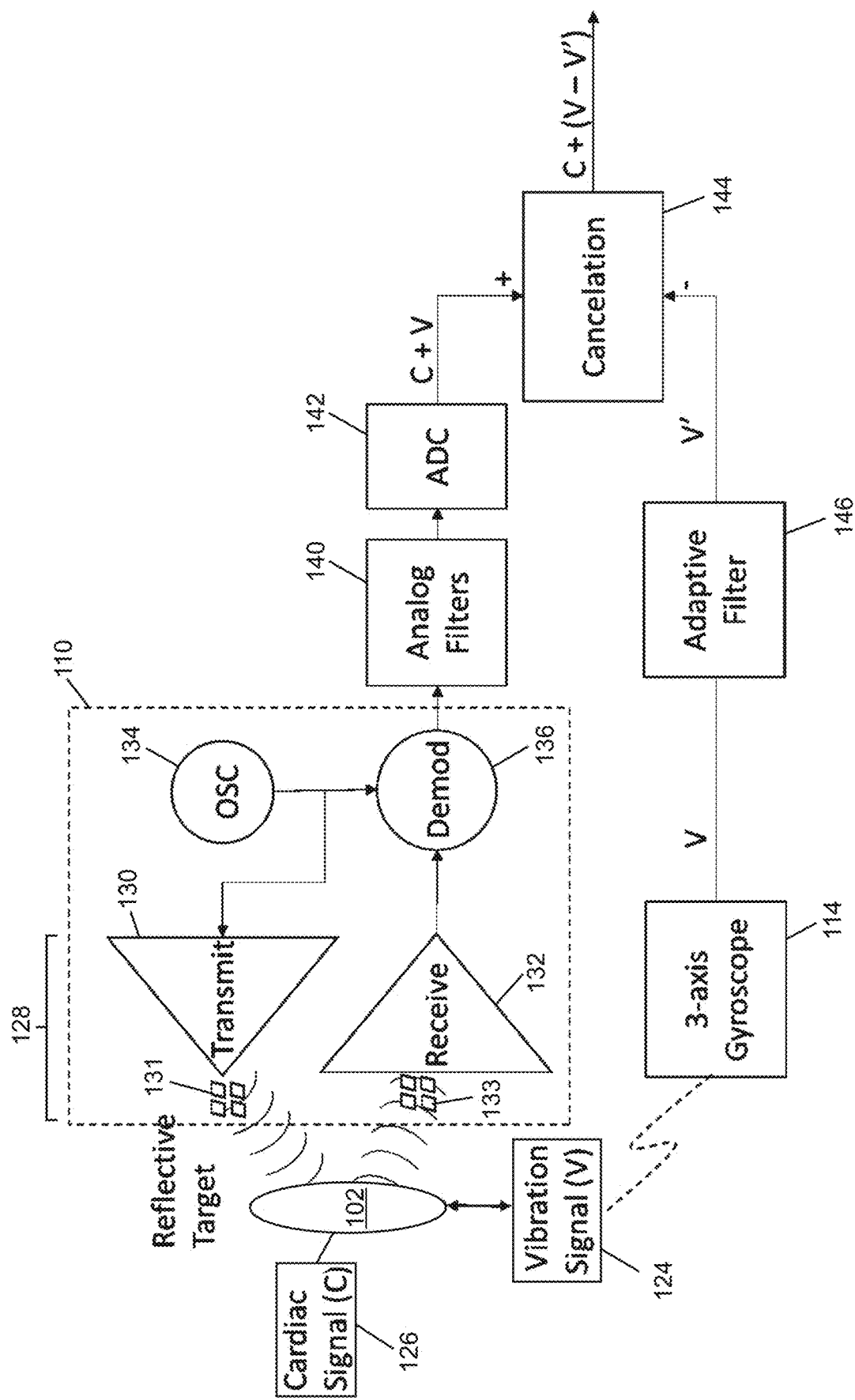
FIG. 2 is a schematic diagram of the heart rate detection system of FIG. 1A, illustrating exemplary signal processing components for vibration cancellation coupled to a radio frequency (RF) transceiver and a gyroscope.

FIG. 2 is a schematic diagram of the heart rate detection system of FIG. 1A, illustrating exemplary signal processing components for vibration cancellation coupled to the RF sensor 110 and the gyroscope. The RF sensor 110 includes an RF transceiver 128 that incorporates at least one RF transmitter 130 (with an associated transmit antenna 131) and at least one RF receiver 132 (with an associated receive antenna 133) arranged in sufficient proximity to the subject 102 under test to enable an RF signal from the RF transmitter 130 to impinge on tissue of the subject 102 under test, and to permit a reflection of the transmitted RF signal (e.g., a response signal) to be received by the RF receiver 132. Multiple RF transmitters 130 and/or RF receivers 132 may be used, such as may be useful to mitigate motion artifacts and/or detect multiple subjects in a sensing area. Although the RF transmitter 130 and RF receiver 132 are illustrated as being spatially separated, such components 130, 132 may be grouped or otherwise packaged in a single component or assembly.

The RF transceiver 128 is in communication with additional RF components (as described in further detail in FIGS. 3A and 3B) to facilitate transmission and detection of RF signals. An RF signal generated by the RF transmitter 130 may include a continuous wave signal, and is preferably a microwave signal (e.g., preferably in an unregulated RF band such as 900 MHz, 2.4 GHz, 5.8 GHz, 10 GHz, 24 GHz, 60 GHz, or 77 GHz). The invention is not limited to use of continuous wave signals, since pulsed signals and/or other signals used in conventional radar (including Doppler radar) systems may be used, as will be apparent to one skilled in the art.

In certain embodiments, the RF transmitter 130 is coupled to a directional patch antenna for a transmit antenna 130, which may be fabricated as copper on a controlled impedance substrate (e.g., PCB) (e.g., 112 as shown in FIG. 1A). The patch antenna 130 is designed for a particular direction and field of view that is appropriate to cover the area (width and distance) where the subject 102 under test is located, and will vary based upon each particular system's configuration. The RF receiver 132 is coupled to a receive antenna 133, which may be a separate instance of the same or different field of view. In embodiments using a pulsed radar, a single antenna can act as the transmit antenna 131 and the receive antenna 133.

The transmit antenna 131 is fed via 50-ohm matched transmission lines to the RF transceiver 128. On the transmit side, an oscillator 134 is arranged to generate an oscillating wave signal at a desired frequency (e.g., 10 GHz). This frequency may be static in the case of continuous wave (CW), or may be chirped in the case of frequency-modulated CW (FM-CW). The oscillator 134 may further be coupled to a splitter (not shown) to divide the oscillating wave signal, a circulator (not shown) to promote one-way flow of the oscillating wave signal within the RF transceiver, and one or more amplifiers (not shown) to provide an amplified oscillating wave signal to the transmit antenna 130. This transmit signal is passed through the transmit antenna 130, and propagates through free space and any obstructions until it hits a surface (e.g., the subject 102) that reflects the signal. The reflected signal will be modulated by the motion of the object. Free space path loss and other obstructions will attenuate the signal as a function of the square of the distance in each direction.

A small portion of the reflected signal, further reduced by the radar cross section of the subject 102, hits the effective aperture of the receive antenna 133 and will pass through a 50-ohm matched transmission line to the RF receiver 132 of the RF transceiver 128. The RF transceiver 128 will heterodyne or direct convert the response signal with the local oscillator 134, and output the baseband signal in phase and quadrature components of the response signal. This signal contains the modulation present as a result of the properties of the reflected object in addition to a phase shift based on distance, and a coherent and non-coherent phase noise component consisting of the vehicle engine and road noise interference.

These quadrature outputs are sent to an analog front end (e.g., one or more analog filters 140) for amplification, as further discussed below with respect to FIGS. 3A and 3B. The signal is then passed to an analog to digital converter (ADC) 142, which provides the signal to a processing device 144 for vibration cancellation and heart rate extraction.

In parallel, the gyroscope 144 is mounted to the same substrate as the RF transceiver 128 and connected to a processor (not shown). The processor samples the vibration signal (V) 124 detected by the gyroscope 144 at a multiple of the heart rate being sampled by the ADC 142 described above. The vibration signal will vary depending on whether the vehicle (e.g., car) engine is off, idling or accelerating, along with the random effects of road noise, tire noise, and bumps on the road.

The signal coming out of the RF sensor 110 has both the cardiac signal (C) being detected from the subject 102 under test and the vibration signal (V)–(C+V). The signal coming out of the gyroscope 114 is only the vibration signal (V) of the vehicle. Therefore, the vibration signal (V) can be subtracted from the RF sensor signal (C+V) leaving behind the cardiac signal (C), thus cancelling out the interference of the vibration noise.

Figures 3A, 3B:
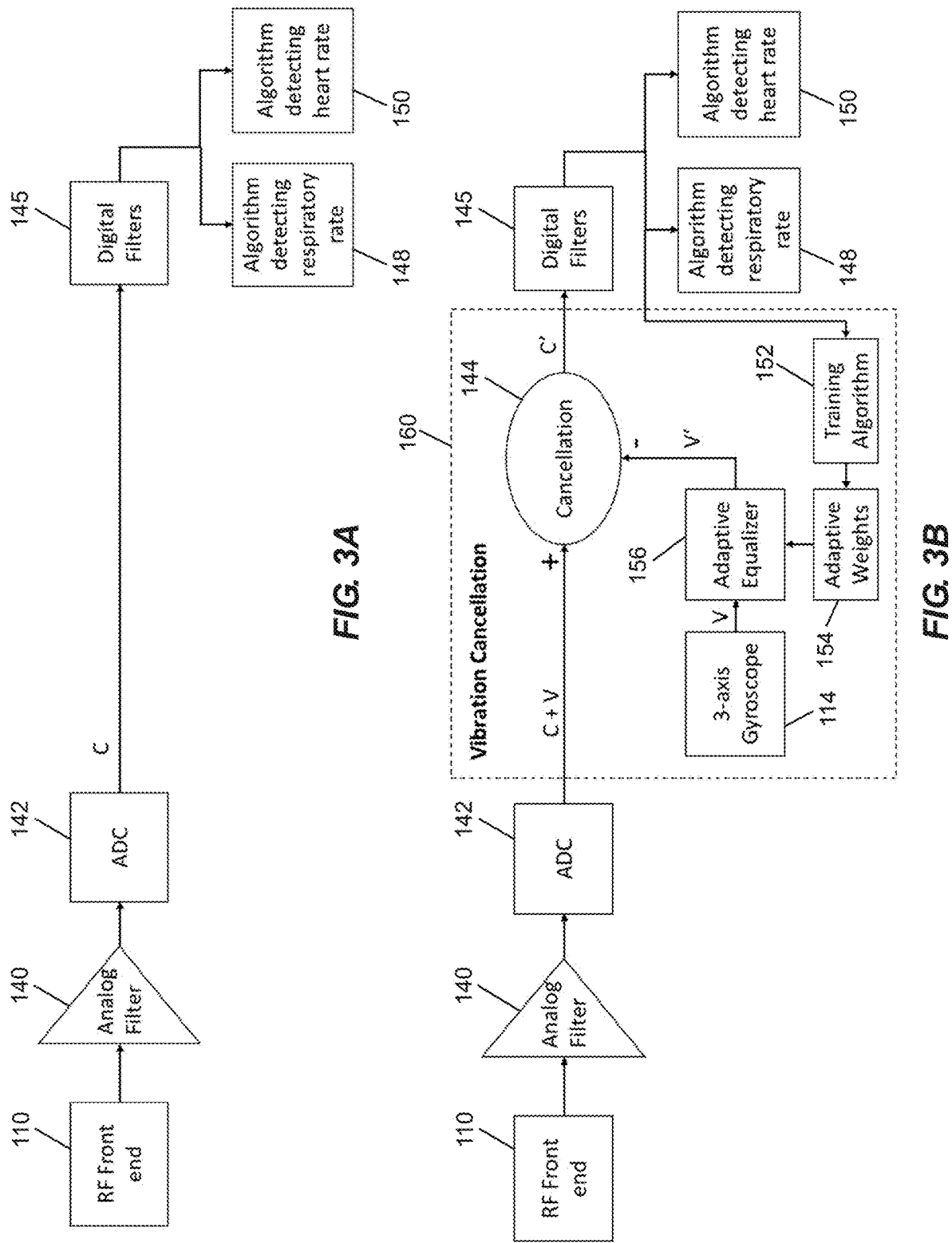
FIG. 3A is a schematic diagram of the heart rate detection system of FIG. 1A without vibration compensation.
FIG. 3B is a schematic diagram of the heart rate detection system of FIG. 3A with vibration compensation.

FIG. 3A is a schematic diagram of the heart rate detection system of FIG. 1A without vibration compensation. In certain embodiments, the analog front end 110 receives and amplifies a response signal (which includes a cardiac signal of the subject under test) from an output of the RF transceiver (e.g., a quadrature output of the RF transceiver). The baseband signal has been severely attenuated due to free space path loss, and low radar cross section of the subject under test. The signal is too low to be detected directly and must be amplified for analysis. The analog amplification is done utilizing ultra-low noise amplifiers in a multi-stage design. An analog gain of between 10× and 100× is used to cover the ranges of interest for a heart rate and respiration detection system. The gain stage also implements hardware filtering (i.e., using analog filter 140) to limit the frequency response of the analyzed signal to the areas of interest where the cardiac signal exits.

The signal is then passed to the ADC 142, which in certain embodiments is an n-bit ADC (e.g., at least 12 bit) and sampled at a rate of at least 50 samples per second. The ADC 142 stores the samples of the in-phase and quadrature components. In certain embodiments, the processor (not shown) reads these samples from the registers of the ADC 140, when the ADC 140 signals data is available via its interrupt signal. The data samples are then passed onto an algorithm engine which processes the data for heart rate extraction. An algorithm engine may incorporate digital filters 145 and at least one processor that executes a first algorithm 148 detecting respiratory rate, and that executes a second algorithm 150 detecting heart rate.

FIG. 3B is a schematic diagram of the heart rate detection system of FIG. 3A with vibration compensation. With continuing reference to FIG. 2 and FIG. 3B, vibration cancellation is achieved through addition of the gyroscope 114 mounted to the same substrate as the RF transceiver. The gyroscope 114 provides a motion signal on a parallel path to the received signal path that is acted upon by the RF front end 110, the analog filter 140, and the ADC 142. In certain embodiments, the gyroscope 114 is a 3-axis gyroscope and is connected to the processor (not shown) via a bus, such as an I2C or SPI bus. The processor samples the vibration signal (V) detected by the gyroscope 114 at a multiple of the heart rate being sampled by the ADC 142 described above. The vibration signal will vary depending on whether the vehicle (e.g., car) engine is off, idling or accelerating, along with the random effects of road noise, tire noise, and bumps on the road.

As described above, the vibration signal (V) from the gyroscope 114 can be subtracted from the RF sensor signal (C+V) leaving behind the cardiac signal (C), thus cancelling out the interference of the vibration noise. However, the vibration signal may not have the same filter and gain characteristics as the vibration signal going through the received signal path from the RF transceiver (128 in FIG. 2)—therefore the vibration signal will need to be equalized to match the channel distortion that it goes through compared to the RF sensor signal. This is done through an adaptive equalizer filter 156, which may be embodied in a multi-tap finite impulse response (FIR) or infinite impulse response (IIR) filter whose function is to compensate for the channel distortion occurring between the RF sensor path and the gyroscope path.

The term adaptive filter implies changing the characteristic of a filter in some automated fashion to obtain the best possible signal quality in spite of changing signal/system conditions. Adaptive filters are usually associated with the broader topic of statistical signal processing. The operation of signal filtering by definition implies extracting something desired from a signal containing both desired and undesired components. With linear FIR and IIR filters the filter output is obtained as a linear function of the observation (signal applied) to the input. An optimum linear filter in the minimum mean square sense can be designed to extract a signal from noise or interference by minimizing the error signal formed by subtracting the filtered signal from the desired signal. For noisy interfering signals with time varying statistics, this minimization process is often done using an adaptive filter. For statistically stationary inputs this solution is known as a Wiener Filter, such as illustrated in FIG. 4.

Figure 4:
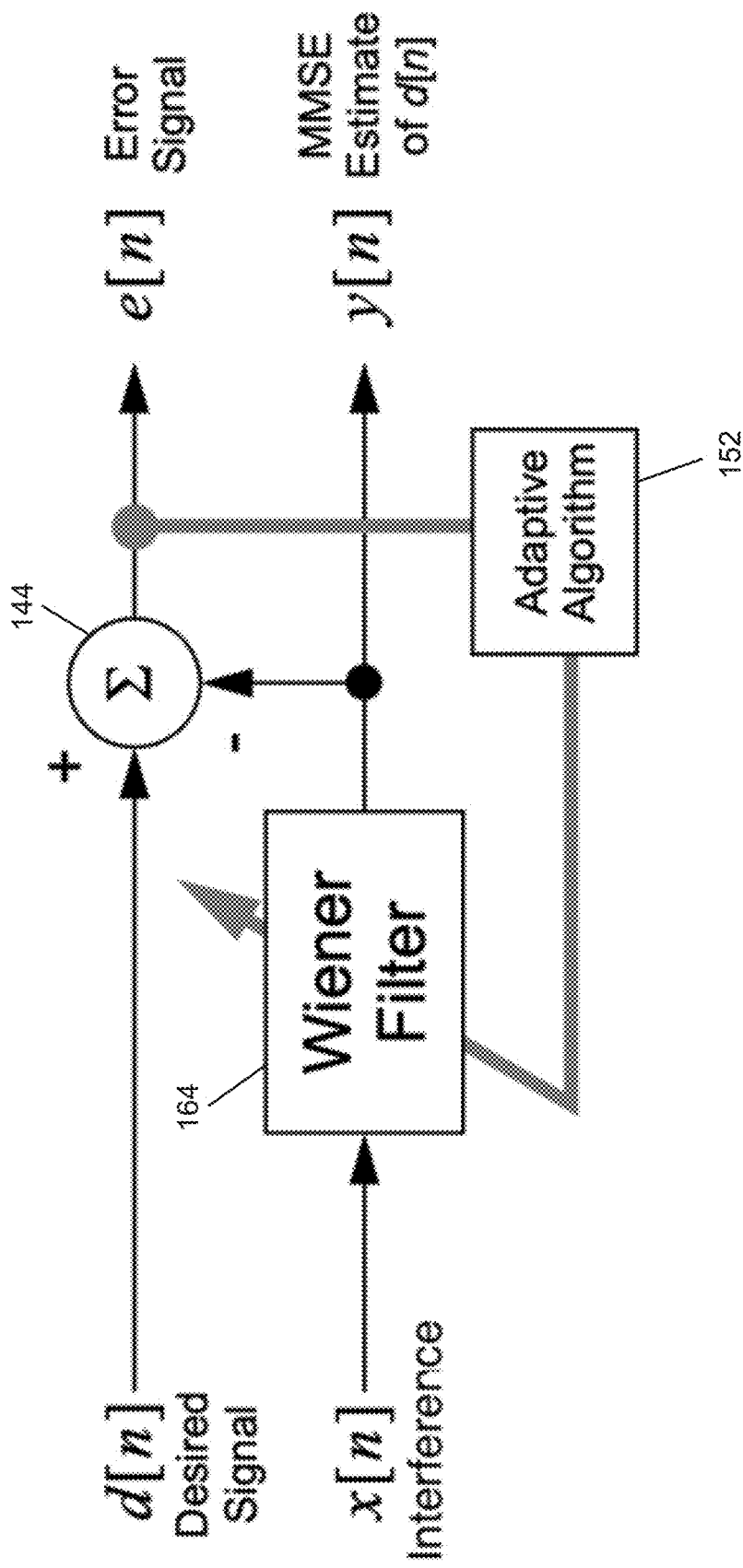
FIG. 4 is a schematic diagram of an exemplary adaptive equalizer for the heart rate detection system of FIG. 1A, implemented as a Wiener filter.

FIG. 4 is a schematic diagram of an exemplary adaptive equalizer for the heart rate detection system of FIG. 1A, implemented as a Wiener filter 164. In this regard, an M tap Wiener filter is of the form:

$$y[n] = \sum_{m=0}^{M-1} w_m x[n-m] \qquad \text{Equation 1}$$

For a linear FIR filter, the quality of the filtered or estimated signal y[n] is determined from the error sequence e[n]=d[n]−y[n]. The weights ($w_m$, m=0, 1, ..., M−1) are chosen such that:

$$E\{e^2[n]\} = E\{(d[n]-y[n])^2\} \qquad \text{Equation 2}$$

is minimized (e.g., the minimum mean-squared error (MMSE) is obtained).

Optimal weights for the filter can be found by setting:

$$\frac{\partial}{\partial w_m} E\{e^2[n]\} = 0, m = 0, 1, \ldots, M-1 \qquad \text{Equation 3}$$

From the orthogonality principle, weights are chosen such that the error e[n] is orthogonal to the observations (e.g., data), such that:

$$E\{x[n-k](d[n]-y[n])\} = 0, k=0,1, \ldots, M-1 \qquad \text{Equation 4}$$

This results in a filter that is optimum in the sense of MMSE.

With continued reference to FIG. 3B, in certain embodiments, tap weights (also referred to as adaptive weights) 154 for the adaptive equalizer 156 are trained to obtain correct tap weights. The training can be performed by a training algorithm 152 after installation of the RF sensor (110 in FIG. 1) in the vehicle seat. With no passenger sitting in the seat, the car is turned on and the tap weights 154 of the adaptive filter 156 are adapted via a cost function-driven gradient descent training algorithm 152 to produce the least amount of noise at the output of the cancellation (e.g., the cost function). This training algorithm 152 is utilized to perform training again with the car being driven and new tap weights 154 are generated. A least mean squares (LMS) algorithm 152 can be run to optimize the tap weight 154 of the adaptive filter 156. The algorithm can now use these tap weights 154 to cancel the path difference between the RF sensor and gyroscope based on the state of the car as detected by the average signal level of vibration detected from the gyroscope 114.

Gradient descent (and stochastic gradient descent) is an optimization algorithm used to find the values of parameters (e.g., coefficient) of a function (e.g., ƒ(•) that minimizes a cost function (cost). Gradient descent and stochastic gradient descent are best used when the parameters cannot be calculated analytically (e.g., using linear algebra) and must be searched for by an optimization algorithm. Almost every machine learning algorithm has an optimization algorithm at its core. The goal is to continue to try different values for the coefficients, evaluate their cost and select new coefficients that have a slightly better (lower) cost. Repeating this process enough times will lead to optimizing the values of the coefficients that result in the minimum cost.

In both gradient descent and stochastic gradient descent, a set of parameters is updated in an iterative manner to minimize an error function. With gradient descent, the machine learning algorithm runs through all the samples in a training set to do a single update for a parameter in a particular iteration. However, with stochastic gradient descent, the machine learning algorithm can use only one or a subset of samples of the training set to do the update for a parameter in a particular iteration. Thus, if the number of training samples is large (especially if very large), using gradient descent may take too long because in every iteration, when updating the values of the parameters the algorithm must run through the complete training set. In contrast, using stochastic gradient descent will be faster because only one training sample (or a subset of training samples) is used and the algorithm begins improving immediately from the first sample.

Stochastic gradient descent often converges much faster compared to gradient descent but the error function is not as well minimized as in the case of gradient descent. However, in an exemplary aspect the close approximation from stochastic gradient descent for the parameter values is sufficient to reach optimal values.

In certain examples, the gradient descent procedure begins with initial values for the coefficient or coefficients for the function. These could be 0.0 or a small random value (e.g., coefficient=0.0). The cost of the coefficients is evaluated by plugging them into the function and calculating the cost:

$$\text{cost} = f(\text{coefficient}) \qquad \text{Equation 5}$$

or $$\text{cost} = \text{evaluate}(f(\text{coefficient})) \qquad \text{Equation 6}$$

The derivative of the cost (e.g., the slope of the function at a given point) is calculated. With the derivative, the slope is known such that the direction to move the coefficient values (e.g., positive or negative) is determined in order to get a lower cost on the next iteration:

$$\Delta = \text{derivative}(\text{cost}) \qquad \text{Equation 7}$$

With the direction known, the coefficient values can be updated. A learning rate parameter (e.g., α) must be specified that controls how much the coefficients can change on each update:

$$\text{coefficient} = \text{coefficient} - (\alpha \Delta) \qquad \text{Equation 8}$$

This process is repeated until the cost of the coefficients (cost) is 0.0 or otherwise sufficiently close to zero.

With continued reference to FIG. 3B, once the vibration cancelation has been completed, the post processed samples are filtered (by filtering element(s) 145) to remove out-of-band noise and phase noise components, as well as compensate for the phase delay based on the distance to the target object. Since the cancellation cannot be 100%, the vibration signal left not cancelled is V'. The processed signal sent to extract the heart rate is (C+V'), where V' should be a very small value now.

The samples are then passed to an algorithm 150 that detects heartbeats. In certain embodiments, heartbeats are determined via a ballistocardiogram (BCG) like waveform that exists on either the in-phase or quadrature channels or both depending upon the distance to the target. In certain embodiments, an AI engine analyzes the incoming signal and extracts each BCG waveform amidst high amounts of variation in the BCG pulse itself as well as perturbations in the waveform from other sources such as motion, multi-path reflections, or noise in the frequency band of the RF interface. Another algorithm 148 may be used to detect respiratory rate.

Figure 5A:
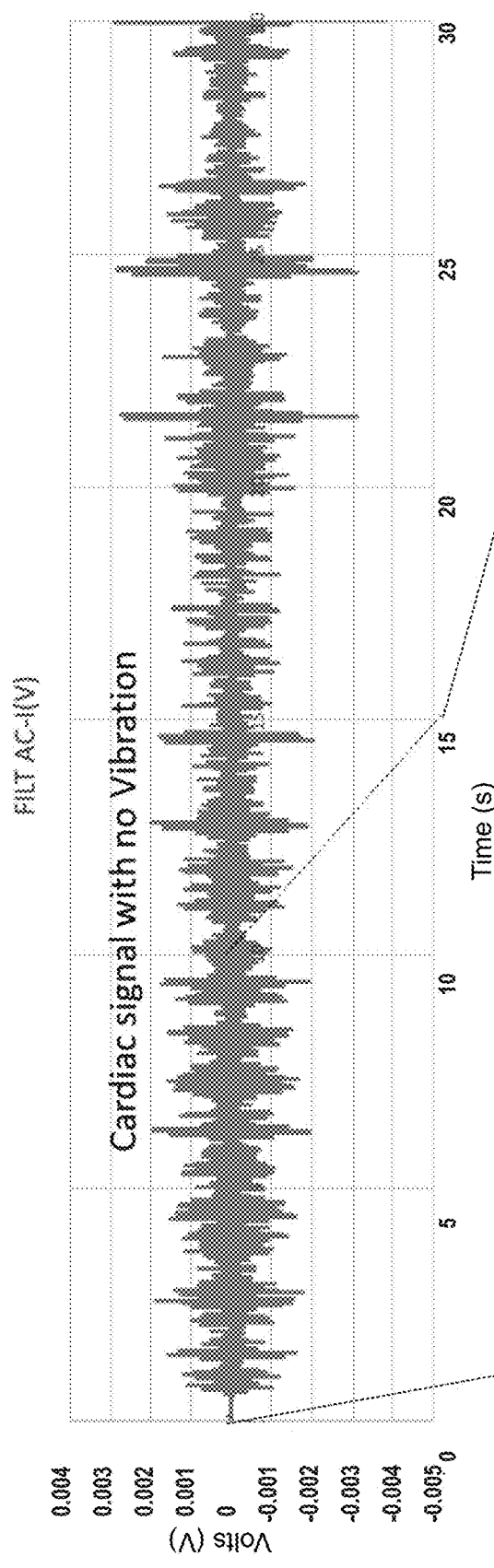
FIG. 5A is a graphical representation of a cardiac signal without vibration received by the heart rate detection system of FIG. 1A.

FIG. 5A is a graphical representation of a cardiac signal without vibration received by the heart rate detection system of FIG. 1A.

Figure 5B:
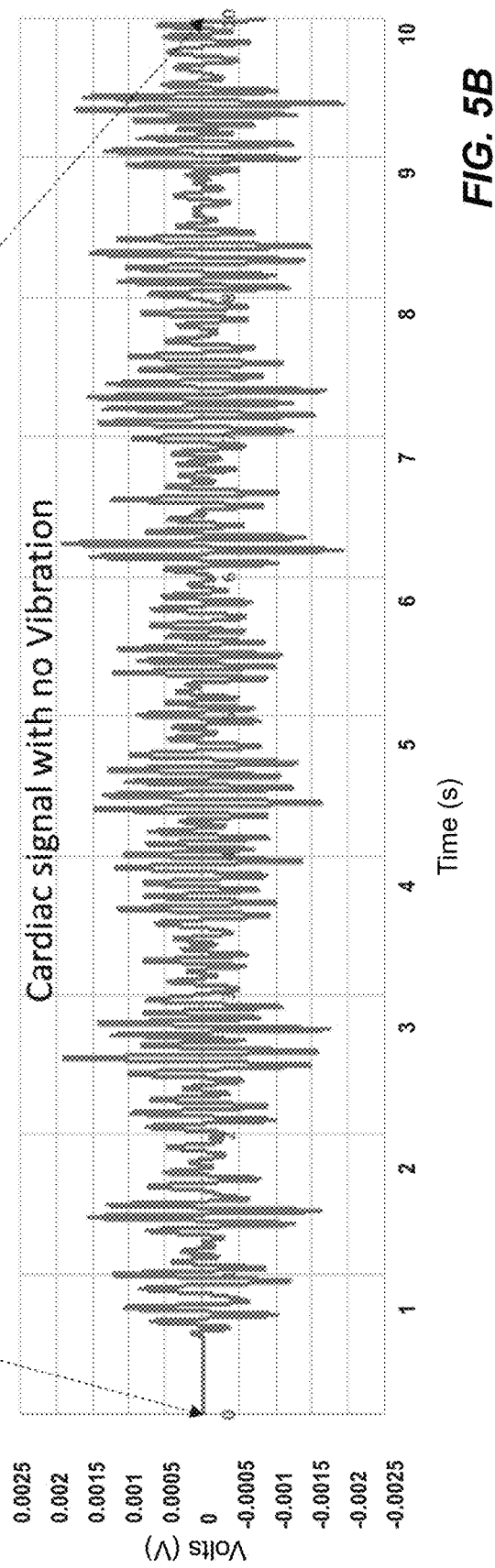
FIG. 5B is a magnified view of a portion of the cardiac signal representation of FIG. 5A.

FIG. 5B is a magnified view of a portion of the cardiac signal of FIG. 5A.

Figure 6:
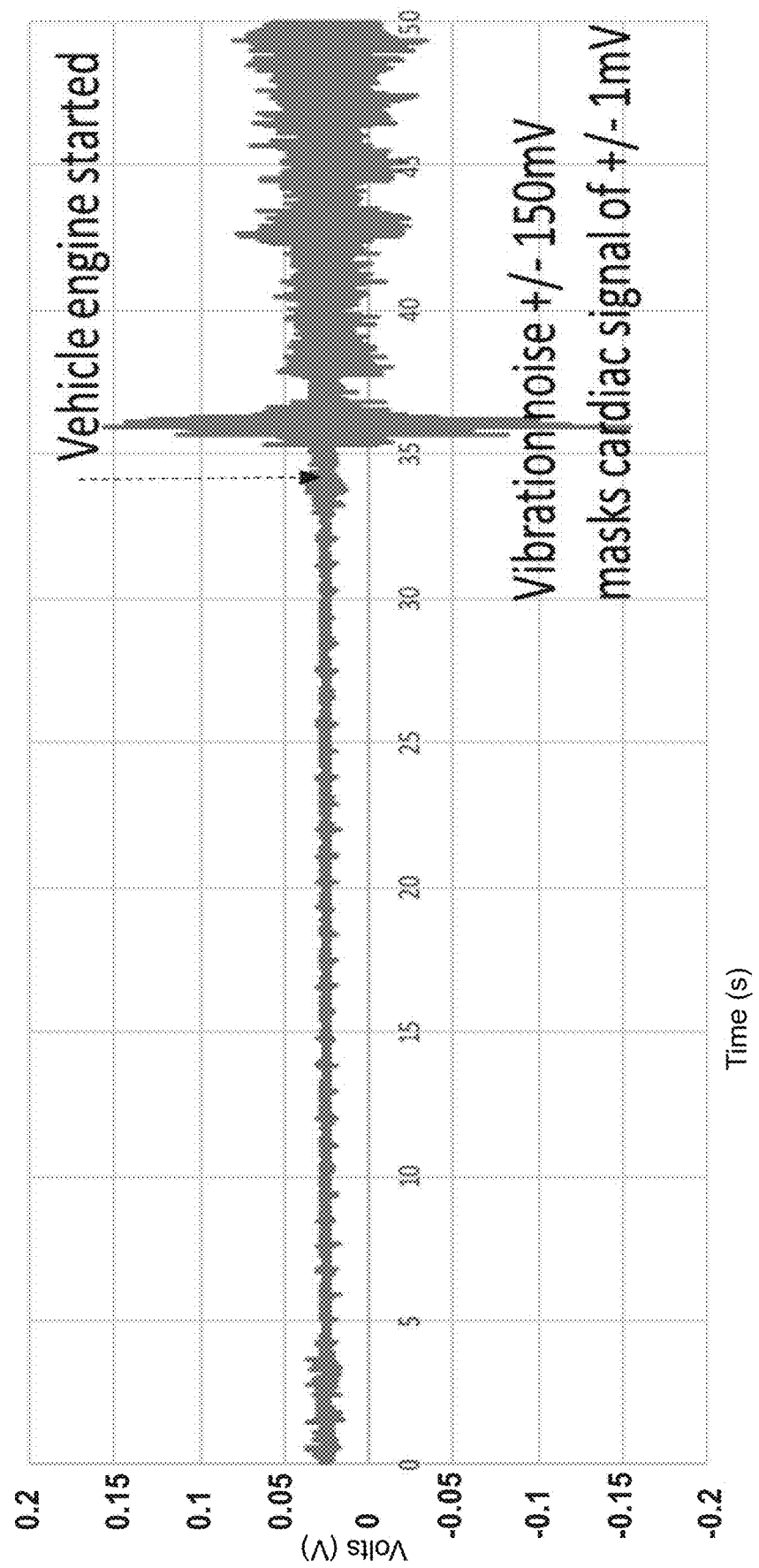
FIG. 6 is a graphical representation of another cardiac signal received by the heart rate detection system of FIG. 1A with a vibration component from engine noise when the vehicle is started masking the cardiac signal.

FIG. 6 is a graphical representation of another cardiac signal received by the heart rate detection system of FIG. 1A, with a vibration component from engine noise when the vehicle is started that masks the cardiac signal.

Figure 7A:
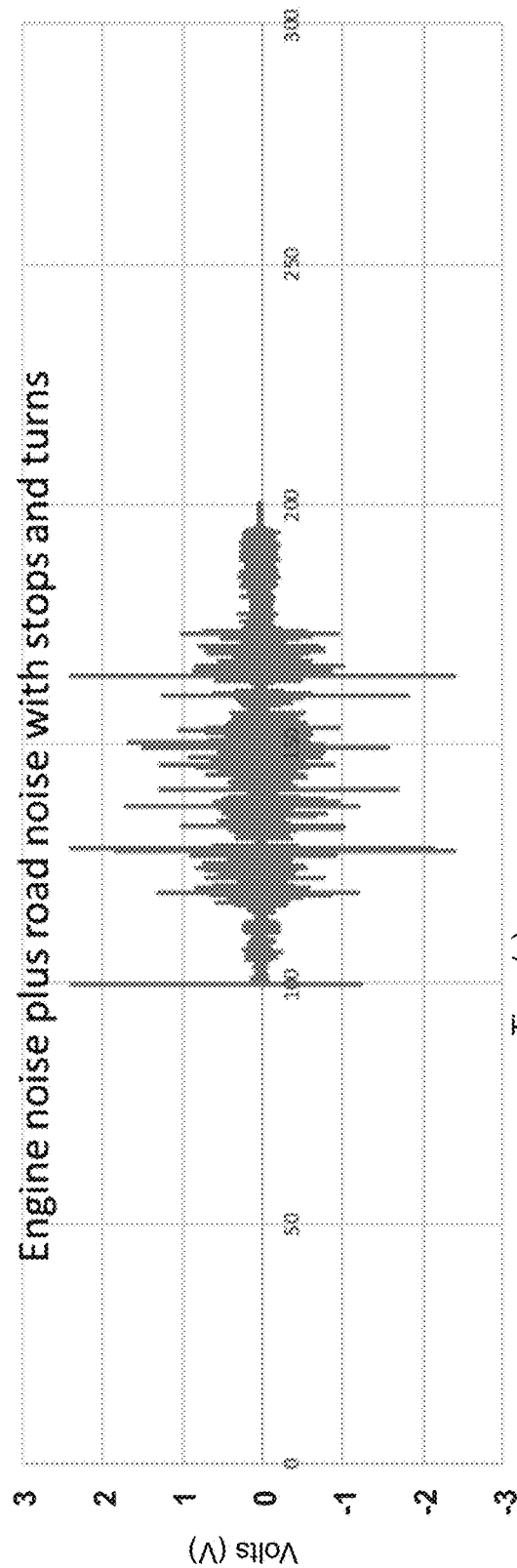
FIGS. 7A and 7B are graphical representations of another cardiac signal received by the heart rate detection system of FIG. 1A with a vibration component from the vehicle operating and being driven masking the cardiac signal.
Figure 7B:
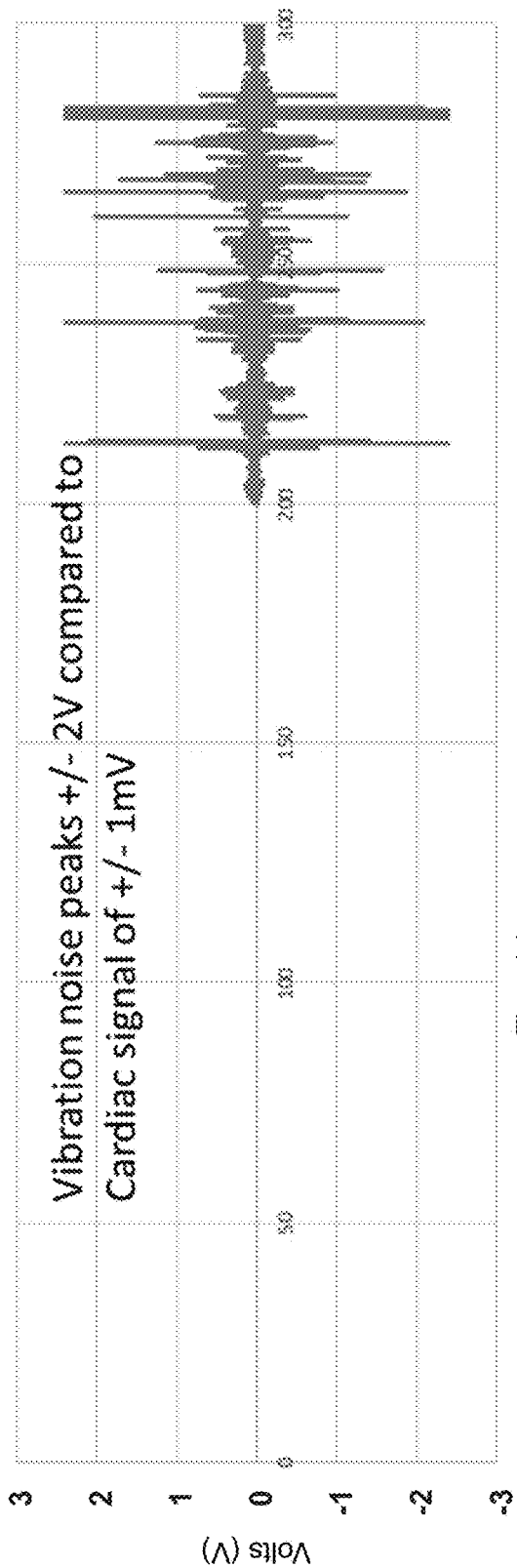

FIGS. 7A and 7B are graphical representations of another cardiac signal received by the heart rate detection system of FIG. 1A with a vibration component from the vehicle operating and being driven masking the cardiac signal.

Figure 8:
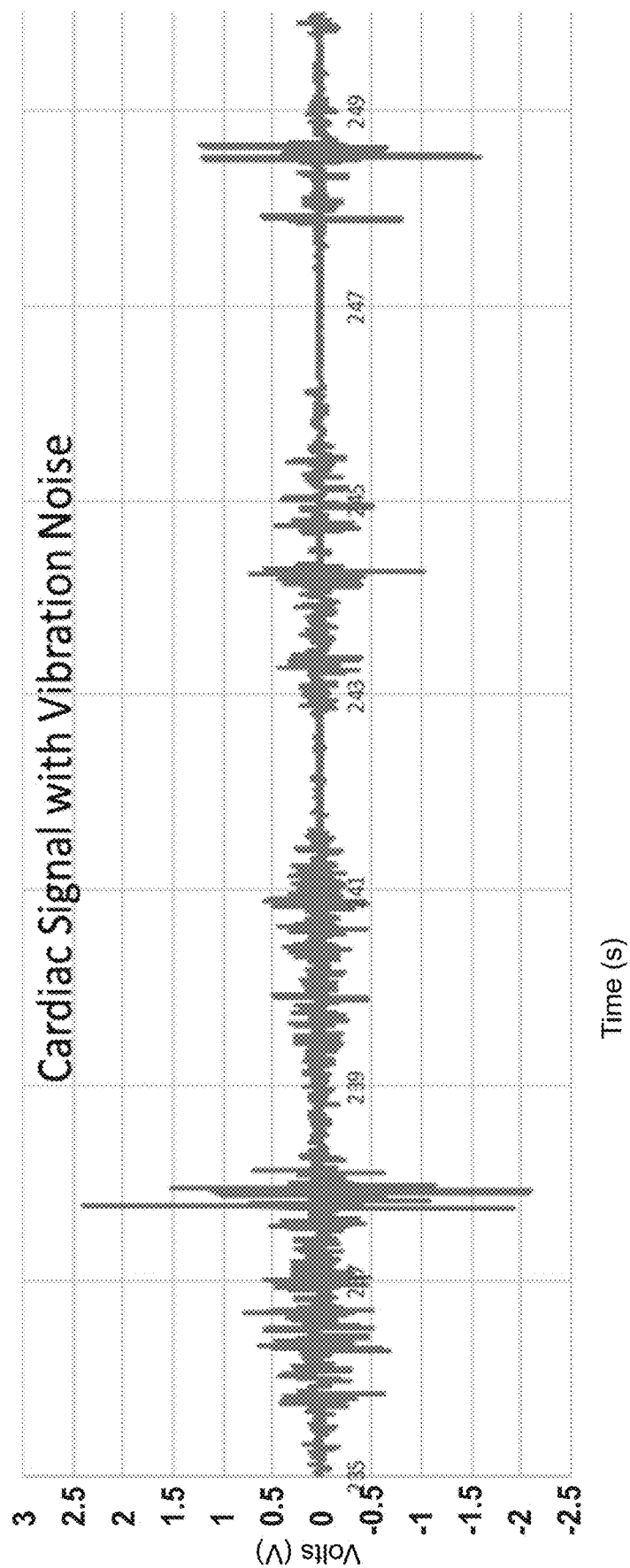
FIG. 8 is a graphical representation of another cardiac signal received by the heart rate detection system of FIG. 1A with a vibration component from the vehicle operating and being driven masking the cardiac signal.

FIG. 8 is graphical representation of another cardiac signal received by the heart rate detection system of FIG. 1A with a vibration component from the vehicle operating and being driven masking the cardiac signal.

Figure 9:
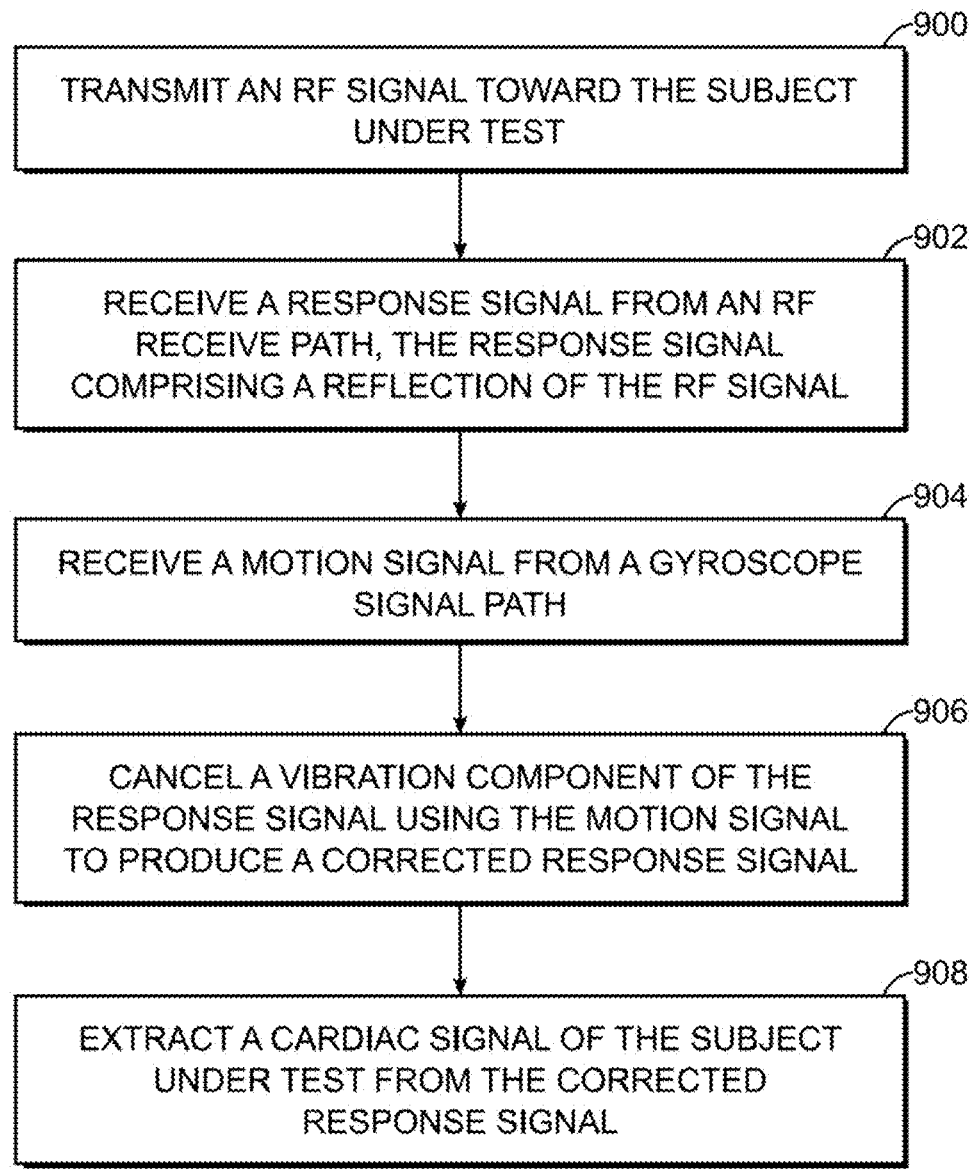
FIG. 9 is a flow diagram illustrating a process for detecting heart rate of a subject under test in a vehicle.

FIG. 9 is a flow diagram illustrating a process for detecting heart rate of a subject under test in a vehicle. The process begins at operation 900, with transmitting an RF signal toward the subject under test. The process continues at operation 902, with receiving a response signal from an RF receive signal path, the response signal comprising a reflection of the RF signal. The process continues at operation 904, with receiving a motion signal from a gyroscope signal path. The process continues at operation 906, with cancelling a vibration component of the response signal using the motion signal to produce a corrected response signal. The process continues at operation 908, with extracting a cardiac signal of the subject under test from the corrected response signal.

Although the operations of FIG. 9 are illustrated in a series, this is for illustrative purposes and the operations are not necessarily order dependent. Some operations may be performed in a different order than that presented. For example, in certain embodiments the response signal and the motion signal are received at a same time. Further, processes within the scope of this disclosure may include fewer or more steps than those illustrated in FIG. 9.

Figure 10:
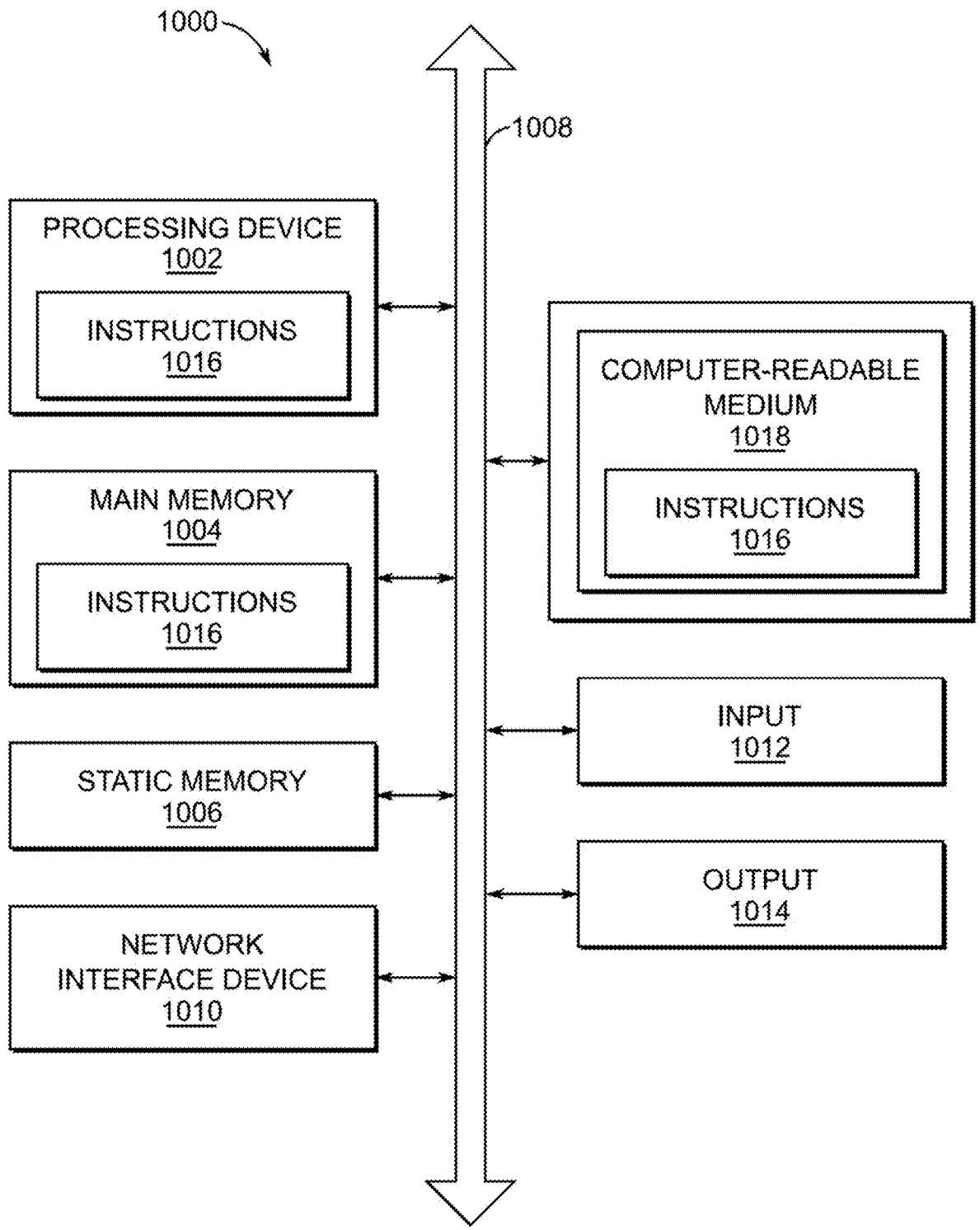
FIG. 10 is a schematic diagram of a generalized representation of an exemplary computer system that could be used to perform any of the methods or functions described above, such as detecting heart rate of a subject under test in a vehicle.

FIG. 10 is a schematic diagram of a generalized representation of an exemplary computer system 1000 that could be used to perform any of the methods or functions described above, such as detecting heart rate of a subject under test in a vehicle. In some examples, the RF sensor and/or the processing device are implemented as the computer system 1000. In this regard, the computer system 1000 may be a circuit or circuits included in an electronic board card, such as, a PCB, a server, a personal computer, a desktop computer, a laptop computer, an array of computers, a personal digital assistant (PDA), a computing pad, a mobile device, or any other device, and may represent, for example, a server or a user's computer.

The exemplary computer system 1000 in this embodiment includes a processing device 1002 or processor, a main memory 1004 (e.g., read-only memory (ROM), flash memory, dynamic random access memory (DRAM), such as synchronous DRAM (SDRAM), etc.), and a static memory 1006 (e.g., flash memory, static random access memory (SRAM), etc.), which may communicate with each other via a data bus 1008. Alternatively, the processing device 1002 may be connected to the main memory 1004 and/or static memory 1006 directly or via some other connectivity means. In an exemplary aspect, the processing device 1002 could be used to perform any of the methods or functions described above.

The processing device 1002 represents one or more general-purpose processing devices, such as a microprocessor, central processing unit (CPU), or the like. More particularly, the processing device 1002 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1002 is configured to execute processing logic in instructions for performing the operations and steps discussed herein.

The various illustrative logical blocks, modules, and circuits described in connection with the embodiments disclosed herein may be implemented or performed with the processing device 1002, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 1002 may be a microprocessor, or may be any conventional processor, controller, microcontroller, or state machine. The processing device 1002 may also be implemented as a combination of computing devices (e.g., a combination of a DSP and a microprocessor, a plurality of microprocessors, one or more microprocessors in conjunction with a DSP core, or any other such configuration).

The computer system 1000 may further include a network interface device 1010. The computer system 1000 also may or may not include an input 1012, configured to receive input and selections to be communicated to the computer system 1000 when executing instructions. The input 1012 may include, but not be limited to, a touch sensor (e.g., a touch display), an alphanumeric input device (e.g., a keyboard), and/or a cursor control device (e.g., a mouse). In an exemplary aspect, the RF transceiver and/or the gyroscope of FIG. 1A are inputs 1012 to the computer system 1000. The computer system 1000 also may or may not include an output 1014, including but not limited to a display, a video display unit (e.g., a liquid crystal display (LCD) or a cathode ray tube (CRT)), or a printer. In some examples, some or all inputs 1012 and outputs 1014 may be combination input/output devices.

The computer system 1000 may or may not include a data storage device that includes instructions 1016 stored in a computer-readable medium 1018. The instructions 1016 may also reside, completely or at least partially, within the main memory 1004 and/or within the processing device 1002 during execution thereof by the computer system 1000, the main memory 1004, and the processing device 1002 also constituting computer-readable medium. The instructions 1016 may further be transmitted or received via the network interface device 1010.

While the computer-readable medium 1018 is shown in an exemplary embodiment to be a single medium, the term "computer-readable medium" should be taken to include a single medium or multiple media (e.g., a centralized or distributed database, and/or associated caches and servers) that store the one or more sets of instructions 1016. The term "computer-readable medium" shall also be taken to include any medium that is capable of storing, encoding, or carrying a set of instructions for execution by the processing device 1002 and that causes the processing device 1002 to perform any one or more of the methodologies of the embodiments disclosed herein. The term "computer-readable medium" shall accordingly be taken to include, but not be limited to, solid-state memories, optical medium, and magnetic medium.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for detecting heart rate of a subject under test in exposure to transit-induced vibration, the method comprising:
   transmitting a radio frequency (RF) signal toward the subject under test;
   receiving a RF response signal from an RF receive signal path, the RF response signal comprising a reflection of the RF signal;
   receiving a motion signal from a gyroscope signal path;
   equalizing the gyroscope signal path to the RC receive signal path utilizing an adaptive equalizer;
   cancelling a vibration component of the RF response signal using the motion signal to produce a corrected response signal; and
   extracting a cardiac signal of the subject under test from the corrected response signal;
   wherein the method comprises one of the following items (i) or (ii):
   (i) the subject under test is in a vehicle, the transmitting of the RF signal is performed with a vehicle-mounted RF transmitter, the receiving of the RF response signal is performed with a vehicle-mounted RF receiver, the receiving of the motion signal from the gyroscope signal path is performed with a vehicle-mounted gyroscope element, and the method comprises calibrating the adaptive equalizer with the vehicle operating and with no human subject present to further equalize the gyroscope signal path to the RF receive signal path; or
   (ii) the method further comprises digitally filtering, by the adaptive equalizer, the motion signal from the gyroscope signal path using a set of tap weights trained with a learning algorithm.

2. The method of claim 1, wherein:
   the subject under test is not in a vehicle;
   the transmitting of the RF signal is performed with a RF transmitter that is held by the subject, worn by the subject, or placed proximate to the subject;
   the receiving of the RF response signal is performed with a RF receiver that is held by the subject, worn by the subject, or placed proximate to the subject; and
   the receiving of the motion signal from the gyroscope signal path is performed with a gyroscope element that is held by the subject, worn by the subject, or placed proximate to the subject.

3. The method of claim 1, wherein the method comprises item (i), namely, the subject under test is in a vehicle, the transmitting of the RF signal is performed with a vehicle-mounted RF transmitter, the receiving of the RF response signal is performed with a vehicle-mounted RF receiver, the receiving of the motion signal from the gyroscope signal path is performed with a vehicle-mounted gyroscope element, and the method comprises calibrating the adaptive equalizer with the vehicle operating and with no human subject present to further equalize the gyroscope signal path to the RF receive signal path.

4. The method of claim 3, further comprising recalibrating the adaptive equalizer with the vehicle operating and a human subject present.

5. The method of claim 1, wherein the method comprises item (ii), namely, digitally filtering, by the adaptive equalizer, the motion signal from the gyroscope signal path using a set of tap weights trained with a learning algorithm.

6. The method of claim 5, wherein the subject under test is in a vehicle, the transmitting of the RF signal is performed with a vehicle-mounted RF transmitter, the receiving of the RF response signal is performed with a vehicle-mounted RF receiver, and the receiving of the motion signal from the gyroscope signal path is performed with a vehicle-mounted gyroscope element.

7. The method of claim 1, wherein the RF receive signal path comprises an RF antenna, an analog front end, and an analog to digital converter (ADC).

8. A radio frequency (RF) sensor, comprising:
   a substrate;
   an RF transceiver mounted to the substrate;
   a gyroscope mounted to the substrate;
   an adaptive equalizer coupled to the gyroscope; and
   a processing device coupled to the RF transceiver and the gyroscope, the processing device configured to:
      cause the RF transceiver to transmit an RF signal toward a subject under test;
      receive a RF response signal comprising a reflection of the RF signal from the RF transceiver;
      monitor a motion signal from the gyroscope;
      cancel a vibration component of the RF response signal using the motion signal from the gyroscope to produce a corrected response signal; and
      extract a cardiac signal of the subject under test from the corrected response signal;
   wherein the adaptive equalizer is configured to apply a distortion to the motion signal, the distortion to the motion signal being matched to a receive path between an antenna coupled to the RF transceiver and the processing device.

9. The RF sensor of claim 8, further comprising an analog front end coupled to the RF transceiver and configured to receive, filter, and amplify an RF signal received by the transceiver to provide an analog response signal.

10. The RF sensor of claim 9, further comprising an analog to digital converter (ADC) coupled to the analog front end and configured to digitally convert the analog response signal to the response signal provided to the processing device.

11. The RF sensor of claim 8, wherein the distortion to the motion signal is further matched to a distortion of an analog front end coupled to the RF transceiver.

12. The RF sensor of claim 8, wherein the adaptive equalizer is trained after installation of the RF sensor in a vehicle.

13. The RF sensor of claim 12, wherein training the adaptive equalizer comprises minimizing a difference between the vibration component from the receive path and the motion signal provided to the processing device with the vehicle operating and no human subject present.

14. The RF sensor of claim 12, wherein training the adaptive equalizer comprises minimizing a difference between the vibration component from the receive path and the motion signal provided to the processing device with the vehicle operating and a human subject present.

15. A heart rate detection system, comprising:
a vehicle comprising a seat;
a radio frequency (RF) sensor coupled to the seat, the RF sensor comprising:
   a substrate;
   an RF transceiver mounted to the substrate;
   a gyroscope mounted to the substrate;
   an adaptive equalizer coupled to the gyroscope; and
   a processing device coupled to the RF transceiver and the gyroscope, the processing device configured to:
      cause the RF transceiver to transmit an RF signal toward a subject under test;
      receive a RF response signal comprising a reflection of the RF signal from the RF transceiver;
      monitor a motion signal from the gyroscope;
      cancel a vibration component of the RF response signal using the motion signal from the gyroscope to produce a corrected response signal; and
      extract a cardiac signal of the subject under test from the corrected response signal;
   wherein the adaptive equalizer is configured to apply a distortion to the motion signal matched to a receive path between an antenna coupled to the RF transceiver and the processing device.

16. The heart rate detection system of claim 15, further comprising a network interface device configured to couple to a vehicle computer, a relay, or a sensor.

17. The heart rate detection system of claim 15, wherein the adaptive equalizer comprises a multi-tap digital filter trained after installation of the RF sensor in the vehicle.

18. The heart rate detection system of claim 17, wherein the processing device is further configured to adjust the distortion applied to the motion signal based on a vehicle status signal received from the vehicle computer, the relay, or the sensor.

* * * * *